(12) United States Patent
Presti

(10) Patent No.: US 10,478,408 B2
(45) Date of Patent: Nov. 19, 2019

(54) COMBINATION TREATMENTS FOR OPIOID CRISIS

(71) Applicant: Michael Presti, Jacksonville, OR (US)

(72) Inventor: Michael Presti, Jacksonville, OR (US)

( * ) Notice: Subject to any disclaimer, the term of this patent is extended or adjusted under 35 U.S.C. 154(b) by 0 days.

(21) Appl. No.: 15/881,475

(22) Filed: Jan. 26, 2018

(65) Prior Publication Data

US 2019/0231719 A1    Aug. 1, 2019

(51) Int. Cl.
| | | |
|---|---|---|
| *A61K 31/145* | (2006.01) | |
| *A61K 31/485* | (2006.01) | |
| *A61P 25/36* | (2006.01) | |
| *A61K 31/4468* | (2006.01) | |
| *A61P 25/04* | (2006.01) | |
| *A61K 31/137* | (2006.01) | |

(52) U.S. Cl.
CPC .......... *A61K 31/145* (2013.01); *A61K 31/137* (2013.01); *A61K 31/4468* (2013.01); *A61K 31/485* (2013.01); *A61P 25/04* (2018.01); *A61P 25/36* (2018.01)

(58) Field of Classification Search
CPC ............................ A61K 31/485; A61K 31/145
See application file for complete search history.

(56) References Cited

U.S. PATENT DOCUMENTS 5,140,032 A * 8/1992 Radecki ................. A61K 31/55
514/221
2010/0311704 A1    12/2010 Gooberman

FOREIGN PATENT DOCUMENTS

CA    2414500 A1    6/2004

OTHER PUBLICATIONS

Specka et al., Clinical Neuropharmacology, 2014, 37(6):161-165.*
Brien et al. Trends in Pharmacological Scieneces, 1985, 6:477-480 (abstract).*
Koppaka et al. Pharmacol Rev, 2012, 64(3): 520-539.*
Listings of opiates from recoveryconnection.com., 2016.*
International Search Report and Written Opinion for PCT/US2019/014659 dated Apr. 10, 2019; 8 pages.
Deserthopethreament.com "What Happens When You Mix Alcohol with Prescription Opiates?" <https://deserthopetreatment.com/drug-overdose/mix-with-alcohol/> Sep. 29, 2016; Section "Overdose".
Bemben "CDC recommends limiting duration of opioid therapy for acute pain" Pharmacy Today vol. 22, Issue 9, p. 46, para 1-2; Sep. 2016.

* cited by examiner

*Primary Examiner* — Rei Tsang Shiao
(74) *Attorney, Agent, or Firm* — Schwabe Williamson & Wyatt, PC

(57) ABSTRACT

A method of reducing the risk of medication-related overdose, death, or other injury associated with inappropriate consumption of alcohol in conjunction with prescription opioid analgesics, comprising: administering a combination medication having an effective amount of one or more opioid medications, and an effective amount of one or more aldehyde dehydrogenase inhibitors, in order to provide the powerful analgesic effects of the opioid in conjunction with a substance that prevents concomitant alcohol consumption, thereby reducing the risk of alcohol mediated opioid overdose or death. A combination medication, including an effective amount of one or more opioid medications, and an effective amount of one or more aldehyde dehydrogenase inhibitors and a pharmaceutically acceptable carrier.

16 Claims, No Drawings

COMBINATION TREATMENTS FOR OPIOID CRISIS

FIELD OF THE DISCLOSURE

The present disclosure relates to methods for reducing the risk of medication-related overdose, death, or other injury associated with inappropriate consumption of alcohol in conjunction with prescription opioid analgesics.

BACKGROUND

Opioid analgesics (e.g., morphine, methadone, hydrocodone, oxycodone, hydromorphone, fentanyl, oxymorphone, codeine, etc.) are one of the most widely abused classes of prescription medications. These medications are known to be dangerous, and put users at risk for adverse health effects, among the most concerning of which are the complications of overdose, including death. These risks are increased exponentially when the medications are misused, such as when taken along with alcohol.

Excessive alcohol consumption also accounts for a significant health burden, and is common among groups that report high rates of prescription drug abuse. And when taken with opioids, it is well-established that alcohol increases central nervous system depression and the risk for overdose. Despite these known risks, patients exhibit very high rates of non-adherence with medical recommendations to avoid alcohol consumption when taking opioid medications. In fact, per estimates from the National Institute of Drug Abuse (NIDA), roughly 21-29% of patients prescribed opioids for chronic pain misuse them, and a large proportion of this misuse relates to co-administration of these medications with alcohol.

To quantify alcohol involvement in opioid medication-related deaths, and to inform prevention efforts, the U.S. Center for Disease Control and Prevention (CDC) recently analyzed data for drug-related deaths that involved opioids and alcohol in 13 states. The analysis showed that alcohol was involved in 22.1% of opioid drug-related deaths. These data are highly consistent with an analysis which evaluated the prevalence and characteristics of opioid-related deaths involving alcohol in Ontario, Canada, which showed that approximately 20% of fatal opioid overdoses involved alcohol. Similarly, another recent analysis showed that Americans with chronic non-cancer pain managed with opioids and a previous diagnosis of alcohol abuse or dependence had 5 times the rate of opioid overdose, 2.3 times the rate of accidents, and 1.2 times the rate of injury, as well as higher all-cause health care costs.

Based on these and other data, the CDC recently concluded that interventions to reduce the abuse of alcohol in conjunction with opioid medications are needed. However, the current standard of care for prevention of co-administration of alcohol with opioids is limited to patient counseling and random urine drug testing, which as evidenced by the data outlined above, represents an ineffective measure. A more definitive solution for preventing co-administration of alcohol with opioid medications is therefore essential for enhancing the safety of these inherently dangerous medications.

SUMMARY

Disclosed is a method of reducing the chances of alcohol mediated opioid overdose or death. In embodiments, the method includes administering a combination medication, for example as a single pill, that includes an effective amount of one or more opioid medications, and an effective amount of one or more aldehyde dehydrogenase inhibitors, in order to provide the powerful analgesic effects of the opioid in conjunction with a substance that prevents concomitant alcohol consumption, thereby reducing the risk of alcohol mediated opioid overdose or death.

Also disclosed is a combination medication that includes an effective amount of one or more opioid medications, and an effective amount of one or more aldehyde dehydrogenase inhibitors and a pharmaceutically acceptable carrier.

In embodiments, the aldehyde dehydrogenase inhibitor includes one or more of disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs NPI-1 and API-1, CVT-10216, DEAB, gossypol, kynurenine tryptophan metabolites, molinate, nitroglycerin, pargyline, active metabolites, analogs, or pharmaceutically acceptable salts thereof. In specific examples, the aldehyde dehydrogenase inhibitor comprises, consists essentially, or consists of disulfiram, active disulfiram metabolites and/or pharmaceutically acceptable salts thereof. In embodiments, the aldehyde dehydrogenase inhibitor consists essentially of disulfiram, active metabolites and/or pharmaceutically acceptable salts thereof.

In embodiments, the one or more opioid medications comprises one or more prescription opioid analgesics. In embodiments, the one or more opioid medications comprises one or more of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, sufentanil, tilidine, and tramadol. In specific examples, the one or more opioid medications comprises, consists essentially of, or consists of morphine, methadone, hydrocodone, oxycodone, oxymorphone, hydromorphone, fentanyl, or codeine.

DETAILED DESCRIPTION

Unless otherwise explained, all technical and scientific terms used herein have the same meaning as commonly understood by one of ordinary skill in the art to which the disclosed subject matter belongs. Definitions of common terms in chemistry terms may be found in The McGraw-Hill Dictionary of Chemical Terms, 1985, and The Condensed Chemical Dictionary, 1981.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description.

Except as otherwise noted, the methods and techniques of the present disclosure are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

In case of conflict, the present specification, including explanations of terms, will control.

To facilitate review of the various embodiments of this disclosure, the following explanations of specific terms are provided:

Administration: To provide or give a subject a composition, such as a pharmaceutical composition including an aldehyde dehydrogenase inhibitor and an opioid medication, by any effective route. Exemplary routes of administration include, but are not limited to, injection (such as subcutaneous, intramuscular, intradermal, intraperitoneal (ip), and intravenous (iv)), oral, sublingual, transdermal, and inhalation routes.

Aldehyde dehydrogenases: Enzymes of enzyme class (EC) 1.2.1.3 that catalyze the oxidation of aldehyde.

Aldehyde dehydrogenase inhibitor: An inhibitor of the enzymatic activity of an aldehyde dehydrogenase. Examples of aldehyde dehydrogenase inhibitors include: disulfiram ([1-diethylthiocarbamoyldisulfanyl-N,N-diethylmethanethioamide]) and active metabolites thereof, such as S-methyl N,N-diethyldithiocarbamate, S-methyl N,N-diethyldithiocarbamate sulfoxide, and S-methyl N,N-diethylthiocarbamate sulfoxide; calcium carbimide, sold as the citrate salt under the trade name Temposil®; coprine and active metabolites thereof, such as 1-amino cyclopropanol; cyanamide and active metabolites thereof, such as HNO; 1-aminocyclopropanol and active metabolites thereof, such as ACP; daidzin; cephalosporins; antidiabetic sulfonyl ureas; metronidazole; ampal and active metabolites thereof, such as thioampal; benomyl (methyl [1-[(butylamino)carbonyl]-1H-benzimidazol-2-yl]carbamate) and active metabolites thereof, such as MBT; citral and active isomers thereof, such as neral and geranial; chloral hydrate; chlorpropamide analogs NPI-1 and API-1, CVT-10216, DEAB, gossypol, kynurenine tryptophan metabolites KA, 3-HK, and 3-HAA; molinate and active metabolites thereof, such as molinate sulfoxide and molinate sulfone; nitroglycerin and active metabolites thereof, such as $NO_3$; pargyline and active metabolites thereof, such as propiolaldehyde; and any other metabolites or analogs exhibiting aldehyde dehydrogenase inhibiting activity.

Contacting: Placement in direct physical association including both in solid or liquid form. Contacting can occur in vivo, for example by administering an agent to a subject.

Inhibiting or treating a disease or a condition: Inhibiting the full development of a disease or condition, for example, in a subject who is in need of an opioid, such as a subject undergoing pain management treatment. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, such as pain, a slower progression of the disease, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology.

Inhibit: To reduce to a measurable extent. For example, to reduce the incident or chance of alcohol mediated or exacerbated opioid induced death and/or overdose.

Opioid medication: Drugs whose primary mode of action is to bind to opioid receptors in the brain, spinal cord, and other areas of the body. Opioid medications work to reduce feelings of pain. Prescription opioids are powerful pain-reducing medications that include prescription oxycodone, hydrocodone and morphine, among others, and have both benefits as well as potentially serious risks. These medications can help manage pain when prescribed for the right condition and when used properly. But when misused or abused, for example when taken in conjunction with alcohol, they can cause serious harm, including overdose and death. Examples of opioid medications include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, sufentanil, tilidine, tramadol, mixtures of any of the foregoing, salts of any of the foregoing, and the like.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Subject: The term "subject" includes both human and veterinary subjects, for example, humans, non-human primates, dogs, cats, horses, rats, mice, and cows. Similarly the term mammal includes both human and non-human mammals. In some embodiments, a subject is a patient, such as patient prescribed one or more opioid medications.

Therapeutic agent or Pharmaceutical agent: A chemical compound, small molecule, or other composition capable of inducing a desired therapeutic or prophylactic effect when properly administered to a subject, for example reducing the chances of alcohol-related opioid death and/or overdose.

Therapeutically effective amount or Effective amount: The amount of agent, such as an aldehyde dehydrogenase inhibitor and an opioid medication, that is sufficient to prevent, treat (including prophylaxis), reduce and/or ameliorate the symptoms and/or underlying causes of any of a disorder or disease, for example to treat, prevent, inhibit, and/or reduce chances of alcohol mediated opioid death and/or overdose.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references. In addition, the materials, methods, and examples are illustrative only and not intended to be limiting.

Overview

Opioids are involved in more overdose deaths than any other drug class. The Centers for Disease Control (CDC) estimates that in 2015 alone, there were over 22,000 deaths involving prescription opioids, equivalent to about 62 deaths per day, and the death rate and rate of other complications associated with opioid overdose have continued to rise at a rapid pace. The risk of opioid overdose is increased exponentially when these medications are misused, such as when taken along with alcohol, as co-consumption of alcohol with opioids results in a synergistic degree of central nervous system and respiratory depression. Despite these known risks, patients exhibit very high rates of non-adherence with medical recommendations to avoid alcohol consumption when taking opioid medications.

Per estimates from the National Institute of Drug Abuse (NIDA), roughly 21-29% of patients prescribed opioids for chronic pain misuse them, and a large proportion of this misuse relates to co-administration of these medications with alcohol. To quantify alcohol involvement in opioid medication-related deaths, the U.S. CDC recently analyzed data for drug-related deaths that involved opioids and alcohol in 13 states, which showed that alcohol was involved in 22.1% of opioid drug-related deaths. These data are highly consistent with a recent analysis which evaluated the prevalence and characteristics of opioid-related deaths involving alcohol in Ontario, Canada, which showed that approximately 20% of fatal opioid overdoses involved alcohol.

In conjunction with the CDC estimates of prescription opioid-related overdose deaths referenced above, these figures suggest that co-consumption of alcohol with prescription opioid medication accounts for nearly 5,000 deaths annually, or more than 13 deaths every day in the United States.

Similarly, another recent analysis showed that Americans with chronic non-cancer pain managed with opioids and a previous diagnosis of alcohol abuse or dependence had 5 times the rate of opioid overdose, 2.3 times the rate of accidents, and 1.2 times the rate of injury, as well as higher all-cause health care costs.

Based on these and other data, the CDC recently concluded that interventions to reduce the abuse of alcohol in conjunction with opioid medications are needed. However, the current standard of care for prevention of co-administration of alcohol with opioids is limited to patient counseling and random urine drug testing, which as evidenced by the data outlined above, represents an ineffective measure.

A more definitive solution for preventing co-administration of alcohol with opioid medications is therefore essential for enhancing the safety of these inherently dangerous medications. The present disclosure addresses the need to prevent co-administration of alcohol with prescription opioids.

Methods of Treatment

Disclosed herein is a method of reducing the chances of alcohol mediated opioid death and/or overdose. The disclosed method involves combining an aldehyde dehydrogenase inhibitor (e.g., disulfiram [1-diethylthiocarbamoyldisulfanyl-N, N-diethylmethanethioamide]) into a combination medication, such as a 'poly-pill', with a prescribed opioid, for example with each of the eight most commonly prescribed opioid pain medication (e.g., hydrocodone, oxycodone, morphine, methadone, codeine, fentanyl, hydromorphone, and oxymorphone) and administering this combination to a subject, such a subject prescribed the opioid medication. Administration of such as combination would enable the delivery of effective opioid-derived analgesia in a manner which prevents co-consumption of alcohol, so as to reduce the risk of alcohol-mediated opioid overdose and/or death.

Existing pharmacotherapies for treating alcoholism include administration of agents that inhibit the enzyme aldehyde dehydrogenase (ALDH), which is involved in the removal of acetaldehyde, a toxic metabolite of alcohol. Although multiple forms of ALDH exist. ALDH-I and ALDH-II are the major enzymes responsible for the oxidation of acetaldehyde. While not being bound by theory, ALDH-I has a higher affinity for acetaldehyde than ALDH-II, and is believed to be the primary enzyme involved in alcohol detoxification. The combination, such as in a poly-pill, of the aldehyde dehydrogenase inhibitor with a prescribed opioid will prevent the co-consumption of alcohol with prescribed opioid medications, because disulfiram and other aldehyde dehydrogenase inhibitors prevent the metabolism of alcohol. Therefore, once an opioid-aldehyde dehydrogenase inhibitor combination medication is administered, the opioid will induce its typical profile of intended analgesic effects, but any subsequent co-consumption of alcohol will result in a strong noxious physiologic reaction to the alcohol.

The disclosed method includes providing and/or administering to a subject a pharmaceutical preparation that includes an effective amount of one or more opioid medications and an effective amount of one or more aldehyde dehydrogenase inhibitors, thereby reducing the chances of the subject succumbing to alcohol mediated opioid death and/or overdose. In embodiments, the method includes the administration of an aldehyde dehydrogenase inhibitor. Examples of aldehyde dehydrogenase inhibitors include, e.g., disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs NPI-1 and API-1, CVT-10216, DEAB, gossypol, kynurenine tryptophan metabolites, molinate, nitroglycerin, pargyline and any active metabolites or analogs exhibiting aldehyde dehydrogenase inhibiting activity.

Patients who consume such inhibitors of ALDH experience mild to severe discomfort if they ingest alcohol. Disulfiram, the best known aldehyde dehydrogenase inhibitor and sold under the tradenames Cronetal™, Abstenil™ Stopetyl™, Contrain™, Antadix™, Anietanol™, Exhoran™, Antabuse™, Etabuse™, Abstinyl™ Thiuranide™, Esperal™, Tetradine™ Noxal™, Tetraeti™, is a potent irreversible inhibitor of ALDH-II that slightly inhibits ALDH-I. Ingestion of alcohol while taking disulfiram and other aldehyde dehydrogenase inhibitors results in the accumulation of aldehydes, which causes tachycardia, flushing, diaphoresis, dyspnea, nausea and vomiting (also known collectively as the disulfiram or disulfiram-ethanol reaction). Disulfiram consumption produces sensitivity to alcohol which results in a highly unpleasant reaction when the subject ingests even small amounts of alcohol. Thus, in specific embodiments, the dehydrogenase inhibitor comprises, consists essentially of, or consists of disulfiram.

In specific embodiments, the method includes the administration of one or more of disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs NPI-1 and API-1, CVT-10216, DEAB, gossypol, kynurenine tryptophan metabolites, molinate, nitroglycerin, pargyline, and/or any active metabolites or analogs exhibiting aldehyde dehydrogenase inhibiting activity. In specific embodiments, the method includes the administration of one or more of disulfiram and/or active metabolites thereof, such as S-methyl N,N-diethyldithiocarbamate, S-methyl N,N-diethyldithiocarbamate sulfoxide, and S-methyl N,N-diethylthiocarbamate sulfoxide.

As disclosed herein the method includes the administration of an opioid medication, such as one or more prescription opioid analgesics. Opioid medications within the present disclosure include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, sufentanil, tilidine, tramadol, mixtures of any of the foregoing, salts of any of the foregoing. Thus, in embodiments, a subject is administered a therapeutically effective amount of one or more of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, sufentanil, tilidine, tramadol, and salts thereof. In embodiments, the subject is not administered propoxyphene, for example propoxyphene is specifically excluded from the combination medication disclosed herein. In specific embodiments, the one or more opioid medications comprises, consists essentially of, or consists of morphine, methadone, hydrocodone, oxycodone, fentanyl, or codeine.

In certain embodiments, the subject is prescribed one or more opioid medications for the management of chronic pain. In certain embodiments, the subject is prescribed one or more opioid medications for the management of acute pain. In certain embodiments, the subject is prescribed one or more opioid medications for the treatment of opioid addiction. In certain embodiments, the subject is prescribed one or more opioid medications for the management of refractory restless legs syndrome or chronic cough.

Therapeutic Formulations

Aspects of the present disclosure further concern a combination medication that includes an aldehyde dehydrogenase inhibitor and an opioid medication.

In embodiments, the combination medication includes an effective amount of one or more aldehyde dehydrogenase inhibitors. In embodiments, the one or more aldehyde dehydrogenase inhibitors is selected from one or more of disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs NPI-1 and API-1, CVT-10216, DEAB, gossypol, kynurenine tryptophan metabolites, molinate, nitroglycerin, pargyline and any active metabolites or analogs exhibiting aldehyde dehydrogenase inhibiting activity. In specific embodiments, the dehydrogenase inhibitor comprises, consists essentially of, or consists of one or more of disulfiram and/or active metabolites thereof, such as S-methyl N,N-diethyldithiocarbamate, S-methyl N,N-diethyldithiocarbamate sulfoxide, and S-methyl N,N-diethylthiocarbamate sulfoxide. In specific embodiments, the dehydrogenase inhibitor comprises, consists essentially of, or consists of disulfiram.

In embodiments, the one or more opioid medications included in the combination medication is selected from alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, sufentanil, tilidine, tramadol, mixtures of any of the foregoing, salts of any of the foregoing, and the like. In embodiments, the combination medication does not include propoxyphene, for example propoxyphene is specifically excluded from the combination medication. In specific embodiments, the one or more opioid medications comprises, consists essentially of, or consists of morphine, methadone, hydrocodone, oxycodone, fentanyl, or codeine.

The method of treatment and pharmaceutical formulations of the present disclosure may further include one or more drugs in addition to the opioid medication and the aldehyde dehydrogenase inhibitor, which additional drug(s) may or may not act synergistically therewith. Thus, in certain embodiments, a combination of two or more opioid medications may be included in the formulation, in addition to the aldehyde dehydrogenase inhibitor. For example, the dosage form may include opioid medications having different properties, such as half-life, solubility, potency, and a combination of any of the foregoing. In yet further embodiments, one or more opioid aldehyde dehydrogenase inhibitors is included and a further non-opioid drug is also included, in addition to the opioid medication. In certain embodiments, such non-opioid drugs would preferably provide additional analgesia, and include, for example, aspirin; acetaminophen; non-sterioidal antiinflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cycooxygenase-II inhibitors ("COX-II inhibitors"); and/or glycine receptor antagonists. Other examples include naloxone (used either to minimize opioid-induced constipation for chronic opioid users or as an abuse-deterrent, to prevent the injection and snorting of oxycodone).

Suitable non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zido-metacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present disclosure, the term "NMDA antagonist" is also deemed to encompass drugs that block a major intracellular consequence of NMDA-receptor activation, e.g. a ganglioside such as $GM_1$ or $GT_{1b}$, a phenothiazine such as trifluoperazine or a naphthalenesulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838, and to treat chronic pain in U.S. Pat. No. 5,502,058.

The treatment of chronic pain via the use of glycine receptor antagonists and the identification of such drugs is described in U.S. Pat. No. 5,514,680. COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311. Certain preferred COX-2 inhibitors include celecoxib (SC-58635), DUP-697, flosulide (CGP-28238), meloxicam, 6-methoxy-2 naphthylacetic acid (6-MNA), MK-966, nabumetone (pro-drug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid medication.

The dosage form of a disclosed pharmaceutical composition will be determined by the mode of administration chosen. For example, in addition to injectable fluids, oral dosage forms may be employed. Oral formulations may be liquid such as syrups, solutions or suspensions or solid such as powders, pills, tablets, or capsules. Methods of preparing such dosage forms are known, or will be apparent, to those skilled in the art.

In embodiments the combination medication is an oral dosage. The oral dosage forms of the disclosure comprise a therapeutically effective amount of an opioid medication, together with an aldehyde dehydrogenase inhibitor, in a therapeutically effective amount that provides a negative, "aversive" physical experience when alcohol is taken in conjunction with the oral dosage form.

The combination of the opioid medication, together with an aldehyde dehydrogenase inhibitor can be employed in admixtures with conventional excipients, i.e., pharmaceutically acceptable organic or inorganic carrier substances suitable for oral administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, for example other analgesic agents. For oral administration, particularly suitable are tablets, dragees, liquids, drops, suppositories, or capsules, caplets and gelcaps. The compositions intended for oral use may be prepared according to any method known in the art and such compositions may contain one or more agents selected from inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. In tablet form, the tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combinations typically include one or more excipients suitable as suspending agents, for example pharmaceutically acceptable synthetic gums such as hydroxypropylmethylcellulose or natural gums. Oily suspensions may be formulated by suspending the above-identified combinations in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed.

An oral dosage form according to the disclosure may be provided as, for example, granules, spheroids, beads, pellets (hereinafter collectively referred to as "multiparticulates"). An amount of the multiparticulates which is effective to provide the desired dose of opioid over time may be placed in a capsule or may be incorporated in any other suitable oral solid form. Alternatively, the oral dosage form may be in the form of a tablet.

Certain embodiments of the pharmaceutical compositions comprising an opioid medication and an aldehyde dehydrogenase inhibitor may be formulated in unit dosage form suitable for individual administration of precise dosages. The amount of active ingredient such as an opioid medication and an aldehyde dehydrogenase inhibitor administered will depend on the subject being treated, the severity of the disorder, and the manner of administration, and is known to those skilled in the art. Within these bounds, the formulation to be administered will contain a quantity of the opioid medication and the aldehyde dehydrogenase inhibitor in an amount effective to achieve the desired effect in the subject being treated.

In particular examples, for oral administration the compositions are provided in the form of a tablet or capsule containing from about 25 mg to 500 mg of the aldehyde dehydrogenase inhibitor (e.g., disulfiram), particularly about 25 mg, about 50 mg, about 75 mg, about 100 mg, about 200 mg, about 250 mg, or about 500 mg of the active ingredient, in combination with the dose of the selected opioid necessary to provide analgesia. This range of doses of disulfiram was selected to facilitate achieving a total daily dose of disulfiram between 250 mg and 500 mg and allow for wide variability in the frequency of the opioid dosing schedules (e.g., the opioid medication can be taken between one and six times daily). In one exemplary oral dosage regimen, a tablet containing about 100 mg of disulfiram in combination with 20 mg of oxycodone is administered every 6 hours (i.e., four times a day), thereby providing a typical total daily dose of disulfiram of about 400 mg. Typical dosage forms of the most common opioid medications (e.g., hydrocodone or oxycodone) are formulated as 5 mg, 10 mg, 20 mg, 40 mg, 80 mg, or 160 mg. Thus combinations of opioid medication with various doses of disulfiram, for example between 25 mg and 500 mg to allow flexibility with regard to the frequency of opioid dosing, are contemplated. Thus for example, in the patient who occasionally takes a single pain tablet on an as-needed basis or who takes a single long-acting opioid tablet on a daily basis, that opioid would be combined with either 250 mg or 500 mg disulfiram. In another patient who takes the opioid analgesic more frequently (e.g., 2-6 times/day), it would be combined with a range of between about 50 mg and about 250 mg disulfiram (e.g., 50, 100, 150, 200, 250 mg), in order to achieve a total daily dose of disulfiram generally between 250 mg and 500 mg. Disulfiram suits this need for flexibility in treating a range of chronic pain patients because it can be administered in a once-daily or a multiple-times daily manner and still be effective for the entire day. Thus, in embodiments, the disulfiram dose is selected which, when the pain medication is taken in the prescribed manner, results in the delivery of a total daily dose of 250-500 mg disulfiram.

In particular examples, for oral administration the compositions are provided in the form of a tablet or capsule containing from about 1.0 to about 200 mg of the opioid medication, particularly about 2.0 mg, about 2.5 mg, 5 mg, about 10 mg, about 20, about, about 50 mg, about 75, about 100, about 125, about 150, about 175 or about 200 mg of the opioid medication (depending on the potency of the particular opioid selected), which for the symptomatic adjustment of the dosage to the subject being treated. In one exemplary oral dosage regimen, a tablet containing from about 1 mg to about 200 mg (such as about 5 mg to about 160 mg) opioid medication is administered between one and six times a day, such as one time, two times, three times, four times, five times, or six times daily.

Single or multiple administrations of the composition comprising the opioid medication, together with an aldehyde dehydrogenase inhibitor can be carried out with dose levels and pattern being selected by the treating physician. Generally, multiple doses are administered. In particular examples, the composition is administered once per day, twice per day, three times per day, four times per day, five times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

Routes of administration useful in the disclosed methods include but are not limited to oral and parenteral routes, such as intravenous (iv), intraperitoneal (ip), rectal, topical, ophthalmic, nasal, and transdermal. Pharmaceutical compositions including opioid medication and an aldehyde dehydrogenase inhibitor can be administered to subjects by a variety of routes. These include oral, nasal (such as intranasal), ocular, buccal, enteral, intravitreal, or other mucosal (such as rectal or vaginal) or topical administration. Alternatively, administration will be by orthotopic, intradermal subcutaneous, intramuscular, parenteral intraperitoneal, or intravenous injection routes. Such pharmaceutical compositions are usually administered as pharmaceutically acceptable compositions that include physiologically acceptable carriers, buffers or other excipients.

An effective amount of an opioid medication and an aldehyde dehydrogenase inhibitor will depend, at least, on the particular method of use, and the manner of administration of the therapeutic composition. A "therapeutically effective amount" of a composition is a quantity of a specified compound sufficient to achieve a desired effect in a subject being treated. Ideally, a therapeutically effective amount of an aldehyde dehydrogenase inhibitor is an amount sufficient to cause a subject to forgo alcohol without a substantial side effect in the subject. Similarly, a therapeutically effective amount of an opioid medication is an amount sufficient to cause the desired effect, such is the prevention of pain without a substantial side effect in the subject.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy.

Typically, preparation of a pharmaceutical composition (for example, for use as a medicament or in the manufacture of a medicament) entails preparing a pharmaceutical composition that is essentially free of pyrogens, as well as any other impurities that could be harmful to humans or animals. The opioid medication and an aldehyde dehydrogenase inhibitor may be included in pharmaceutical compositions (including therapeutic and prophylactic formulations), which are typically combined together with one or more pharmaceutically acceptable vehicles or carriers and, optionally, other therapeutic ingredients.

To formulate the pharmaceutical compositions, the opioid medication and the aldehyde dehydrogenase inhibitor can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The opioid medication and the aldehyde dehydrogenase inhibitor can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, and microspheres.

The opioid medication and the aldehyde dehydrogenase inhibitor can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43: 1-5, 1991), and dispersed in a biocompatible dispersing medium, which yields sustained delivery and biological activity over a protracted time.

The opioid medication and aldehyde dehydrogenase inhibitor can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the opioid medication and the aldehyde dehydrogenase inhibitor can be also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

For prophylactic and therapeutic purposes, the pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein.

Therapeutic compositions that include an opioid medication and an aldehyde dehydrogenase inhibitor can be delivered by way of a pump (see Langer, supra; Sefton, CRC Crit. Ref. Biomed. Eng. 14:201, 1987; Buchwald et al, Surgery 88:507, 1980; Saudek et al, N. Engl. J. Med. 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (Science 249: 1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHRO MED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al, Biopolymers 22:547-556, 1983, poly(2-hydroxyethyl methacrylate)); (Langer et al., J. Biomed. Mater. Res. 15: 167-277, 1981; Langer, Chem. Tech. 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art. In specific examples, the opioid medication and the aldehyde dehydrogenase inhibitor are contained in a time released and/or tamper proof pill and/or capsule. Example or such capsule formulations are well known in the art and include those formulations sold under the tradename OxyContin® and the like. Examples of such time release formulations can be found for example in U.S. Pat. Nos. 5,478,577; 5,681,585, 5,672,360; 5,958,459; 6,103,261; 6,143,332; 5,965,161; 5,958,452, 5,968,551, 5,681,585, 5,811,126, 5,843,480, 5,681,585, 5,811,126, 5,843,480, 5,849,240, 5,866,164, 5,879,705, 5,891,471, 5,914,131, 5,965,163, 5,968,551, 6,103,261, 6,143,322, 6,245,357, 6,261,599, 6,294,195. 6,419,960, 6,696,066, 7,514,100, 7,514,100, 7,829,120, 7,846,476, 7,988,998, 8,071,119, 8,075,872, 8,114,383, 8,114,384, 8,153,149, 8,153,152, 8,153,661, 8,168,217, 8,192,722, 8,231,898, 8,309,060, 8,323,889, 8,354,124, 8,361,499, 8,362,029, 8,372,432, 8,414,919, 8,415,401, 8,420,056, 8,420,120, 8,445,018, 8,486,448, 8,486,449, 8,487,002, 8,529,948, 8,551,520, 8,597,681, 8,609,683, 8,647,667, 8,653,066, 8,658,631, 8,668,929,8,685,447, 8,691,270, 8,715,721, 8,722,086, 8,728,522, 8,741,885, 8,753,665, 8,765,178, 8,795,723, 8,808,740, 8,808,745, 8,815,289, 8,821,929, 8,834,925, 8,846,072, 8,846,086, 8,858,963, 8,871,265, 8,877,241, 8,894,987, 8,894,988, 8,911,719, 8,920,833, 8,920,834, 8,927,013, 8,927,014, 8,927,025, 8,937,097, 8,945,614, 8,951,555, 8,951,556, 8,956,644, 8,962,019, 8,974,821, 8,980,291, 8,987,291, 8,999,961, 9,023,394, 9,023,401, 9,034,376, 9,040,084, 9,044,402, 9,050,335, 9,056,052, 9,056,107, 9,060,940, 9,060,976, 9,084,816, 9,095,614, 9,095,615, 9,101,661, 9,132,096, 9,149,533, 9,161,917, 9,198,861, 9,198,863, 9,198,867, 9,205,055, 9,205,056, 9,216,176, 9,226,901, 9,226,907, 9,233,073, 9,233,160, 9,278,074, 9,278,083, 9,289,391, 9,308,170, 9,308,171, 9,320,717, 9,387,174, 9,387,177, 9,393,206, 9,393,207, 9,399,022, 9,402,813, 9,427,407, 9,433,582, 9,433,625, 9,439,866, 9,452,163, 9,456,985, 9,468,636, 9,486,412, 9,486,413, 9,486,451, 9,492,389, 9,492,390, 9,492,391, 9,492,392, 9,492,393, 9,498,444, 9,498,456, 9,504,681, 9,517,207, 9,517,236, 9,517,271, 9,526,704, 9,526,724, 9,539,328, 9,545,380, 9,545,448, 9,555,113, 9,572,779, 9,572,803, 9,572,804, 9,572,805, 9,572,885, 9,579,285, 9,579,389, 9,592,204, 9,616,030, 9,616,055, 9,629,807, 9,629,837, 9,636,303, 9,642,809, 9,655,853, 9,655,861, 9,655,893, 9,655,894, 9,655,971, 9,662,326, 9,662,399, 9,669,022, 9,669,023, 9,669,024, 9,675,581, 9,675,610, 9,675,611, 9,682,077, 9,693,961, 9,694,080, 9,707,179, 9,707,180, 9,707,224, 9,713,611, 9,730,885, 9,737,490, 9,744,136, 9,744,151, 9,750,701, 9,750,703, 9,750,736, 9,757,341, 9,757,371, 9,763,886, 9,763,933, 9,770,416, 9,770,417, 9,775,808, 9,775,809, 9,775,810, 9,775,811, 9,775,812, 9,775,837, 9,789,104, and 9,789,105.

The subject matter of the present disclosure is further illustrated by the following non-limiting Examples.

EXAMPLES

This example describes exemplary methodology (clinical trial) for testing the efficacy of the disclosed opioid medication aldehyde dehydrogenase inhibitor combination.

A clinical trial is instituted to demonstrate that the combination therapy 1) remains effective as an analgesic and 2) effectively prevents co-administration of alcohol while the patient is using an opioid analgesic (for example, within 12-24 hours following administration of the last dose of the combination medication).

The following represents one of the possible clinical trials that may be instituted to determine efficacy of the combination medication and methods of treatment disclosed herein.

1. Eligibility Assessment and Enrollment
    a. Inclusion Criteria
        i. An individual with a chronic pain condition treated with an opioid analgesic.
        ii. The individual has a prior history of alcohol abuse or is suspected of non-adherence with recommendations to avoid concomitant alcohol consumption while taking opioid medication.
        iii. Age greater than 18 years
        iv. Adults must be able to understand and sign the informed consent document
        v. Patients must have an ECOG performance score of 0-2.
        vi. Patients must have laboratory and physical examination parameters within acceptable limits by standard of practice guidelines.
    b. Exclusion criteria
        Comorbid alcohol dependency (active, not in remission), or opioid use disorder (active, not in remission).
    c. Patient registration
        Patients will be registered on the trial by the principal investigator or their designee using a protocol specific registration form after signing the appropriate informed consent or agreeing by assent.
2. Study Implementation
    This is a prospective study of the efficacy of the combination of an aldehyde dehydrogenase inhibitor, such as disulfiram, and an opioid medication. As both classes of drugs have proven individual efficacy at achieving the desired clinical outcome when administered individually, toxicity studies would be unnecessary. In an example, the study would include 3 groups plus a control: traditional opioid, traditional disulfiram and a comparable opioid-disulfiram combination. Pharmacokinetics would also be performed, as there may need to be some adjustment (for example lowering) in the dosing of certain opioids because their metabolism may be slowed by the disulfiram. Patients are asked to complete a pain rating daily or multiple times per day and are advised/counseled on the importance of alcohol avoidance when taking the pain medication. They are selected/notified randomly at multiple intervals throughout the trial (1-3×/wk) that they must provide a urine or blood sample, and complete surveys regarding their consumption of alcohol during the trial. The groups are then compared for safety and efficacy (in terms of both analgesia and prevention of alcohol co-consumption), side effect profile, and the like.

3. Study Evaluation

Patients will undergo the following evaluations which may be performed within 4 weeks of enrollment:

Detailed History and Physical Examination including, vital signs, ECOG status, demographic information and family history.

Laboratory evaluations: CBC with differential; Chem 20 [Sodium (Na), Potassium (K), Chloride (CI), Total C02 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid]; PT/PTT; Blood alcohol concentration; Urine drug screen (with quantitative and qualitative opioid analyses).

4. Follow-Up Examinations

Patients following evaluations:

a. physical exam to include vital signs and ECOG status;

b. laboratory evaluations: pharmacokinetic analysis of aldehyde dehydrogenase inhibitor and opioid medication.

c. Patients are asked to complete a pain rating daily or multiple times per day d. Patients are advised/counseled on the importance of alcohol avoidance when taking the pain medication.

e. Patients are required to provide urine samples and/or other samples needed to determine blood-alcohol levels at random intervals f. Patients complete a survey/questionnaire about their recent level of alcohol consumption at multiple points over the course of the study.

g. Patients agree to inform study investigators if they experience a complication associated with opioid overdose at any point over the course of the study.

5. Data Collection

Data prior to and during the course of the patient's participation will be collected in order to monitor patient eligibility, and will include review of medical and family history records, blood work, and urinary studies.

a. Toxicity Criteria: This study will utilize the Common Terminology Criteria for Adverse Events (CTCAE) version 4 for toxicity and adverse event reporting. CTCAE version 4 is available on the World Wide Web at ctep.info.nih.gov. All appropriate treatment areas should have access to a copy of the CTCAE version 4.

b. Statistical Considerations: A primary objective of this study is to determine the efficacy of the combination medication to provide the desired opioid effect while reducing the incidence of co-consumption with alcohol.

6. Rationale for Subject Selection

Subjects will be selected for this protocol based on chronic pain condition managed with opioids and alcohol abuse or non-adherence with recommendations to avoid alcohol consumption while taking opioid medication.

7. Data Reporting a. Routine Data Reporting: All details of patient evaluation, management and treatment will be documented in the patient medical record. The following information may be captured on the CRFs: detailed demographic information including family history; and laboratory results).

b. Serious Adverse Event Reporting Requirements: The following events will be reported: all deaths with the exception of those due to progressive disease; all events that are not listed in the consent form and that are possibly, probably or definitely related to the research; all serious adverse events (SAEs) that are not listed in the consent form, but are possibly, probably or definitely related to the research (with the exception of death due to progressive disease). An SAE is defined as an untoward medical occurrence that: resulted in death; was life-threatening; required or prolonged hospitalization; caused persistent or significant disability/incapacity; resulted in congenital anomalies or birth defects; or required intervention to prevent permanent impairment or death.

c. Adverse Event Reporting in the Continuing Review Report: The following events will be presented to provide the information necessary to clearly identify risks to participants and to make a risk:benefit determination: all Grade 2 events that are not in the consent form, but are possibly, probably or definitely related to the research; all Grade 3 and 4 events that are possibly, probably or definitely related to the research; all Grade 5 events regardless of attribution; and all Serious Events regardless of attribution.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of reducing the chances of alcohol mediated opioid overdose or death during maintenance therapy for management of pain, comprising:

selecting a subject for maintenance therapy for management of pain;

administering a single composition to the subject, comprising:

an effective amount of one or more opioid medications for the management of pain; and an effective amount of one or more aldehyde dehydrogenase inhibitors sufficient to prevent alcohol consumption, the one or more aldehyde dehydrogenase inhibitors selected from disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs, (benzoyloxy)[4-chlorophenyl)sulfonyl]carbamic acid 1,1-dimethylethyl ester (NPI-1), 4-chloro-N-ethyl-N-[(propylamino)carbonyl]benzenesulfonamid (API-1), 3-(((3-(4-(methylsulfonamido)phenyl)-4-oxo-4H-chromen-7-yl)oxy)methyl) benzoic acid (CVT-10216), N,N-diethylaminobenzaldehyde (DEAB), gossypol, molinate, nitroglycerin, pargyline, or pharmaceutically acceptable salts thereof, enabling provision of the powerful analgesic effects of the opioid in a manner which prevents concomitant alcohol consumption, thereby reducing the risk of alcohol mediated opioid overdose or death during maintenance therapy for management of pain.

2. The method of claim 1, wherein the aldehyde dehydrogenase inhibitor is disulfiram, or an pharmaceutically acceptable salts thereof.

3. The method of claim 1, wherein the aldehyde dehydrogenase inhibitor is disulfiram, or pharmaceutically acceptable salts thereof.

4. The method of claim 1, wherein the one or more opioid medications is one or more prescription opioid analgesics.

5. The method of claim 1, wherein the one or more opioid medications comprises one or more of alfentanil, allylprodine, alphaprodine, anileridine, benzylmorphine, bezitramide, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, ketobemidone, levorphanol, levophenacylmorphan, lofentanil, meperidine, meptazinol, metazocine, metopon, morphine, myrophine, narceine, nicomorphine, norlevorphanol, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, sufentanil, tilidine, and tramadol.

6. The method of claim 5, wherein the one or more opioid medications is morphine, methadone, hydrocodone, oxycodone, hydromorphone, fentanyl, or codeine.

7. The method of claim 6, wherein the one or more opioid medications consists essentially of one or more of morphine, methadone, hydrocodone, hydromorphone, oxycodone, fentanyl, or codeine.

8. The method of claim 1, wherein the subject is prescribed one or more opioid medications for the management of chronic pain.

9. The method of claim 1, wherein the subject is prescribed one or more opioid medications for the management of acute pain.

10. A method of reducing the chances of alcohol mediated opioid overdose or death during maintenance therapy for management of pain, comprising:
 selecting a subject for maintenance therapy for management of pain;
 administering in a single dose a single combination medication, comprising:
  an effective amount of an opioid medication for the management of pain selected from alfentanil, allylprodine, alphaprodine, anileridine, benzylmorphine, bezitramide, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, ketobemidone, levorphanol, levophenacylmorphan, lofentanil, meperidine, meptazinol, metazocine, metopon, morphine, myrophine, narceine, nicomorphine, norlevorphanol, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, sufentanil, tilidine, and tramadol; and
 an effective amount of one or more aldehyde dehydrogenase inhibitors selected from disulfiram, calcium carbimide, coprine, cyanamide, 1-aminocyclopropanol, daidzin, cephalosporins, antidiabetic sulfonyl ureas, metronidazole, ampal, benomyl, citral and active isomers thereof, chloral hydrate, chlorpropamide analogs, (benzoyloxy)[4-chlorophenyl)sulfonyl]carbamic acid 1,1-dimethylethyl ester (NPI-1), 4-chloro-N-ethyl-N-[(propylamino)carbonyl]benzenesulfonamid (API-1), 3-(((3-(4-(methylsulfonamido)phenyl)-4-oxo-4H-chromen-7-yl)oxy)methyl) benzoic acid (CVT-10216), N,N-diethylaminobenzaldehyde (DEAB), gossypol, molinate, nitroglycerin, pargyline, or pharmaceutically acceptable salts thereof, enabling provision of the powerful analgesic effects of the opioid in a manner which prevents concomitant alcohol consumption, thereby reducing the risk of alcohol mediated opioid overdose or death during maintenance therapy for management of chronic pain.

11. The method of claim 10, wherein the aldehyde dehydrogenase inhibitor is disulfiram, or a pharmaceutically acceptable salts thereof.

12. The method of claim 10 wherein the aldehyde dehydrogenase inhibitor consists essentially of disulfiram, or pharmaceutically acceptable salts thereof.

13. The method of claim 10, wherein the one or more opioid medications comprises morphine, hydrocodone, oxycodone, hydromorphone, fentanyl, or codeine.

14. The method of claim 13, wherein the one or more opioid medications consists essentially of one or more of morphine, hydrocodone, hydromorphone, oxycodone, fentanyl, or codeine.

15. The method of claim 10, wherein the subject is prescribed one or more opioid medications for the management of chronic pain.

16. The method of claim 10, wherein the subject is prescribed one or more opioid medications for the management of acute pain.

* * * * *

UNITED STATES PATENT AND TRADEMARK OFFICE
CERTIFICATE OF CORRECTION

PATENT NO. : 10,478,408 B2
APPLICATION NO. : 15/881475
DATED : November 19, 2019
INVENTOR(S) : Michael Presti Page 1 of 1

It is certified that error appears in the above-identified patent and that said Letters Patent is hereby corrected as shown below:

In the Claims

Claim 2
Column 19, Lines 12-13:
Delete ", or an pharmaceutically acceptable salts thereof" after "disulfiram"

Signed and Sealed this
Twenty-second Day of December, 2020

Andrei Iancu
*Director of the United States Patent and Trademark Office*